United States Patent
Kharas

(10) Patent No.: US 8,344,188 B2
(45) Date of Patent: Jan. 1, 2013

(54) METHODS AND APPARATUS FOR SYNTHESIS OF ALCOHOLS FROM SYNGAS

(75) Inventor: Karl Kharas, Louisville, CO (US)

(73) Assignee: Maverick Biofuels, Inc., Chapel Hill, NC (US)

( * ) Notice: Subject to any disclaimer, the term of this patent is extended or adjusted under 35 U.S.C. 154(b) by 695 days.

(21) Appl. No.: 12/580,022

(22) Filed: Oct. 15, 2009

(65) Prior Publication Data

US 2010/0099927 A1 Apr. 22, 2010

Related U.S. Application Data

(60) Provisional application No. 61/105,858, filed on Oct. 16, 2008.

(51) Int. Cl.
*C07C 29/04* (2006.01)

(52) U.S. Cl. ........ 568/897; 568/895; 568/896; 568/898; 568/909

(58) Field of Classification Search ............ 568/897, 568/895, 896, 898, 909
See application file for complete search history.

(56) References Cited

U.S. PATENT DOCUMENTS

| | | | |
|---|---|---|---|
| 3,352,930 A | 11/1967 | Mention et al. | |
| 4,440,871 A | 4/1984 | Lok et al. | |
| 4,469,903 A | 9/1984 | Schmidt | |
| 5,714,662 A | 2/1998 | Vora et al. | |
| 2004/0116757 A1 | 6/2004 | Van Egmond et al. | |
| 2007/0049647 A1 | 3/2007 | Van Egmond et al. | |

FOREIGN PATENT DOCUMENTS

EP 0955284 A1 11/1999

OTHER PUBLICATIONS

Carle et al., "Synthetic Ethanol Production", Chemistry and Industry, pp. 830-839 (May 12, 1962).
Pio Forzatti et al., "Higher Alcohol Synthesis", Catalysis Reviews, 33:1, 109-168 (Feb. 1, 1991).
Tomoyuki Inui et al., "Reliable Procedure for the Synthesis of Ni-SAPO-34 as a Highly Selective Catalyst for Methanol to Ethylene Conversion", Applied Catalysis A: General, vol. 164, pp. 211-223 (1997).
Stephen Wilson et al., "The Characteristics of SAPO-34 Which Influence the Conversion of Methanol to Light Olefins," Microporous and Mesoporous Materials, vol. 29, pp. 117-126 (1999).

*Primary Examiner* — Elvis O Price
(74) *Attorney, Agent, or Firm* — O'Connor & Company; Ryan P. O'Connor

(57) ABSTRACT

This invention provides a method for producing ethanol and 2-propanol from syngas, the method comprising: (a) converting syngas into methanol using a methanol-synthesis catalyst; (b) converting methanol into ethylene and propylene using a methanol-to-olefins catalyst; and (c) hydrating ethylene into ethanol and propylene into 2-propanol. As taught herein, the combined yield of the ethanol and the 2-propanol from biomass can be at least 100 gallons per dry ton biomass. In certain embodiments, the yield of ethanol is at least 100 gallons per dry ton biomass. In some embodiments, the yield of 2-propanol is at least 50 gallons per dry ton biomass.

42 Claims, 4 Drawing Sheets

METHODS AND APPARATUS FOR SYNTHESIS OF ALCOHOLS FROM SYNGAS

PRIORITY DATA

This patent application claims priority under 35 U.S.C. §120 from U.S. Provisional Patent Application No. 61/105,858 for "METHODS FOR SYNTHESIS OF ALCOHOLS FROM SYNGAS," filed Oct. 16, 2008, the disclosure of which is hereby incorporated by reference herein for all purposes.

FIELD OF THE INVENTION

The present invention generally relates to the field of processes for the chemical conversion of synthesis gas to alcohols, such as ethanol.

BACKGROUND OF THE INVENTION

Synthesis gas (hereinafter referred to as syngas) is a mixture of hydrogen ($H_2$) and carbon monoxide (CO). Syngas can be produced, in principle, from virtually any material containing carbon. Carbonaceous materials commonly include fossil resources such as natural gas, petroleum, coal, and lignite; and renewable resources such as lignocellulosic biomass and various carbon-rich waste materials. It is preferable to utilize a renewable resource to produce syngas because of the rising economic, environmental, and social costs associated with fossil resources.

There exist a variety of conversion technologies to turn carbonaceous feedstocks into syngas. Conversion approaches can utilize a combination of one or more steps comprising gasification, pyrolysis, steam reforming, and/or partial oxidation of a carbon-containing feedstock.

Syngas is a platform intermediate in the chemical and biorefining industries and has a vast number of uses. Syngas can be converted into alkanes, olefins, oxygenates, and alcohols. These chemicals can be blended into, or used directly as, diesel fuel, gasoline, and other liquid fuels. Syngas can also be directly combusted to produce heat and power.

There is commercial interest in producing alcohols from syngas rather than from fermentable sugars. At present, known catalysts for the direct synthesis of higher ($C_{2+}$) alcohols from syngas produce a mixture of alcohols. For example, the product distribution of methanol, ethanol, propanol, butanol, and higher alcohols often follows a Flory-Schulz distribution. Known catalysts for the synthesis of higher alcohols from syngas also can suffer from low productivities and from declining selectivities to higher alcohols as syngas conversion increases. These factors will tend to require recycle of unconverted syngas to the reactor.

Syngas conversion to methanol, on the other hand, is well-known. For example, syngas (usually derived from natural gas) can be catalytically converted to methanol at very high selectivities using a mixture of copper, zinc oxide, and alumina at a temperature of 250° C. and pressures of 750-1500 psi. In addition to $Cu/ZnO/Al_2O_3$, other catalyst systems suitable for methanol synthesis include $ZnO/Cr_2O_3$, $Cu/ZnO$, $Cu/ZnO/Cr_2O_3$, $Cu/ThO_2$, Co/S, Mo/S, Co/Mo/S, Ni/S, Ni/Mo/S, and Ni/Co/Mo/S.

Although methanol can be combusted to produce energy, methanol is not currently acceptable as a liquid transportation fuel except in small quantities, e.g. as a minor additive to gasoline. Methanol can, however, be converted to many other fuels and chemicals. With respect to liquid transportation fuels, methanol can be considered a platform intermediate for producing gasoline and biodiesel. It would be useful to convert methanol to specific oxygenates, such as ethanol, for addition to gasoline. Heavier alcohols can also be valuable for chemical applications, as is known.

In light of the aforementioned needs in the art, what are desired are methods, apparatus, and systems that can cost-effectively produce one or more $C_1$-$C_4$ alcohols, such as ethanol and/or 2-propanol, starting with syngas or methanol. It is sought to overcome the poor selectivities associated with alcohol-synthesis catalysts.

SUMMARY OF THE INVENTION

The present invention addresses the problems in the art by providing methods capable of producing high selectivities to desired alcohols.

In some embodiments, this invention provides a method for producing ethanol and 2-propanol from syngas, the method comprising:

(a) converting syngas into methanol in the presence of a methanol-synthesis catalyst;

(b) converting at least some of the methanol from step (a) into a composition including ethylene and propylene in the presence of a methanol-to-olefins catalyst; and (c) hydrating at least some of the ethylene into ethanol and at least some of the propylene into 2-propanol.

In some embodiments, the syngas is derived from biomass. The syngas can be derived, however, from any carbon-containing source.

The methanol-to-olefins catalyst can comprise an aluminosilicate zeolite such as one selected from the group consisting of ZSM-5, ZSM-11, ZSM-12, ZSM-23, ZSM-35, and ZSM-48.

The methanol-to-olefins catalyst can comprise a silicoaluminophosphate such as one selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, and SAPO-56. SAPO-34 is a preferred methanol-to-olefins catalyst.

In some embodiments, the silicoaluminophosphate further includes one or more transition metals, such as (but not limited to) one or more transition metals is selected from the group consisting of Mn, Ni, and Co. Nickel is a preferred transition metal, and a preferred methanol-to-olefins catalyst is Ni-SAPO-34. In some embodiments, the ratio of silicon to the transition metal is selected from about 1 to about 500, such as about 10 to about 200.

In preferred embodiments, step (c) is conducted in the presence of one or more olefin-hydration catalysts, such as one or more olefin-hydration catalysts selected from zeolites, supported acids, acidic resins, and heteropoly acids. One or more olefin-hydration catalysts includes sulfuric acid.

Preferably, one or more olefin-hydration catalysts includes a catalyst selected for ethylene hydration, such as phosphoric acid. Preferably, one or more olefin-hydration catalysts includes a catalyst selected for propylene hydration.

In some embodiments, in step (c), the hydrating of ethylene and propylene is conducted substantially simultaneously. In certain embodiments, the method further includes separating the ethylene from the propylene generated in step (b) and then separately hydrating the ethylene and the propylene during step (c).

In some embodiments, in step (c), hydrating of the propylene is substantially conducted prior to hydrating of the ethylene. In some embodiments, hydrating is conducted in a first reaction zone for converting propylene into 2-propanol and a second reaction zone for converting ethylene into ethanol. Step (b) can further generate butenes which can be hydrated to 2-butanol during step (c).

The first reaction zone can be located in a first reactor and the second reaction zone can be located in a second reactor. Or, both of the reaction zones can be located in a single reactor.

In some embodiments, the temperature within the first reaction zone is lower than the temperature within the second reaction zone. For example, the temperature within the first reaction zone can be selected from about 125-200° C. and the temperature within the second reaction zone can be independently selected from about 200-250° C.

In some embodiments, at least a portion of water produced from reactions during step (b) is used for the hydrating during step (c). In certain embodiments, all or substantially all of the water produced during step (b) is fed for the hydrating during step (c).

In some embodiments, during step (c), one or more dialkyl ethers are generated, and wherein the method further comprises removing at least a portion of the dialkyl ethers during or after step (c).

Methods of the invention can further comprise the step of separating unhydrated olefins from alcohols by distillation. Methods can additionally, or alternatively, comprise the step of separating unhydrated olefins from alcohols by absorption of the alcohols into water.

In some embodiments, the method further comprises the step of separating unhydrated olefins from alcohols by absorption of the alcohols into dimethyl ether. In some embodiments, ethanol and/or the 2-propanol are separated (e.g., distilled) from water. In certain embodiments, ethanol is separated from the 2-propanol.

Some variations of the invention provide a method for producing ethanol and 2-propanol from biomass, the method comprising:
 (a) producing syngas from biomass;
 (b) converting at least some of the syngas into methanol in the presence of a methanol-synthesis catalyst;
 (c) converting at least some of the methanol from step (b) into a composition including ethylene and propylene in the presence of SAPO-34 or Ni-SAPO-34; and
 (d) catalytically hydrating ethylene into ethanol and propylene into 2-propanol,
 wherein the hydrating is conducted in a first reaction zone for converting propylene into 2-propanol and a second reaction zone for converting ethylene into ethanol, and wherein the temperature in the second reaction zone is higher than the temperature in the first reaction zone.

Variations of the present invention also provide a method of separating one or more olefins from one or more alcohols, the method comprising:
 (a) providing a feed stream comprising one or more olefins and one or more alcohols;
 (b) contacting the feed stream with dimethyl ether, under effective conditions for absorption of at least one of the alcohols into the dimethyl ether, to generate a solution of dimethyl ether and the at least one alcohol; and
 (c) removing dimethyl ether from the solution from step (b), to generate a purified alcohol stream comprising the at least one alcohol.

The one or more olefins can include ethylene, propylene, or another olefin. The one or more alcohols can include ethanol, 2-propanol, or another alcohol. In some embodiments, during step (b), ethanol and 2-propanol absorb into the dimethyl ether, and wherein ethylene and propylene do not substantially absorb into the dimethyl ether. In step (c) can include evaporation of dimethyl ether. The olefins can be derived from methanol, and the alcohols can be generated from hydration of the olefins. The dimethyl ether can be derived from the methanol, which can be the same source of methanol as that for generating the olefins.

In step (b), the molar ratio of ethylene to propylene can be greater than about 2, 5, or 10 in various embodiments. After olefin hydration, the combined yield of the ethanol and the 2-propanol from the biomass can be at least 70 gallons per dry ton biomass, at least 100 gallons per dry ton biomass, or at least 120 gallons per dry ton biomass. In certain embodiments, the yield of ethanol is at least 100 gallons per dry ton biomass. In some embodiments, the yield of 2-propanol is at least 50 gallons per dry ton biomass.

The alcohols produced by this invention can be used directly as liquid fuels, or blended into various fuel mixtures. In some embodiments, 2-propanol is blended into gasoline. In some embodiments, ethanol and 2-propanol are blended into gasoline, which can be beneficial to decrease Reid vapor pressure versus a gasoline/ethanol blend because 2-propanol is less volatile than ethanol.

Some variations of the invention convert methanol (from any source) to higher alcohols such as ethanol and 2-propanol. A method is provided for producing ethanol and 2-propanol from methanol, the method comprising:
 (a) converting methanol, in the presence of a methanol-to-olefins catalyst, into a stream including ethylene and propylene;
 (b) feeding the stream from step (a) and water to a first hydration zone under suitable conditions for hydration of propylene to 2-propanol; and
 (c) feeding at least a portion of the output of the first hydration zone, and optionally additional water, to a second hydration zone under suitable conditions for hydration of ethylene to ethanol.

In certain embodiments, the invention provides a method for producing ethanol and 2-propanol from methanol, the method comprising:
 (a) converting methanol, in the presence of SAPO-34 or Ni-SAPO-34, into a stream including ethylene and propylene;
 (b) feeding the stream from step (a) and water to a first hydration zone under suitable conditions for catalytic hydration of propylene to 2-propanol; and
 (c) feeding at least a portion of the output of the first hydration zone and water to a second hydration zone under suitable conditions for catalytic hydration of ethylene to ethanol,
 wherein the temperature in the second hydration zone is higher than the temperature in the first hydration zone.

This invention also provides, in some variations, an apparatus for producing ethanol and 2-propanol from methanol, the apparatus comprising:
 (a) a methanol-to-olefins unit for converting methanol, in the presence of a methanol-to-olefins catalyst, into a first output stream including ethylene and propylene;
 (b) a first hydration zone, optionally containing a first hydration catalyst, and configured for hydrating propylene to 2-propanol;
 (c) a second output stream from the first hydration zone;
 (d) a second hydration zone, optionally containing a second hydration catalyst, and configured for hydrating ethylene to ethanol;
 (e) a third output stream from the second hydration zone;
 (f) means for feeding the first output stream and water to the first hydration zone;

(g) means for feeding the first second stream to the second hydration zone; and (h) means for collecting the ethanol and 2-propanol.

The first hydration zone can located in a first reactor and the second hydration zone can located in a second reactor. Or, both of the hydration zones can be located in a single reactor. In some embodiments, the temperature within the first hydration zone is lower than the temperature within the second hydration zone. For example, the temperature within the first hydration zone can be selected from about 125-200° C. and the temperature within the second hydration zone can be independently selected from about 200-250° C.

The apparatus of some variations of the invention further includes means for separating unhydrated olefins from alcohols. One such means for separating unhydrated olefins from alcohols comprises absorption into dimethyl ether. In some embodiments, the apparatus includes means for separating the ethanol and/or the 2-propanol from water and/or means for separating the ethanol from the 2-propanol.

Other variations of the present invention provide a method for producing ethanol and 2-propanol from methanol, the method comprising:

(a) converting methanol, in the presence of a methanol-to-olefins catalyst, into a stream including ethylene and propylene;

(b) feeding the stream from step (a) and water to a reactive-distillation unit including a first zone containing an propylene-hydration catalyst, a second zone containing a ethylene-hydration catalyst, an overhead stream, and a bottoms stream;

(c) operating the reactive-distillation unit under effective conditions for hydration of propylene to 2-propanol in the first zone and ethylene to ethanol in the second zone; and (d) recovering ethanol and 2-propanol in one or more exit streams from the reactive-distillation unit.

The methanol can be derived from syngas, which can in turn be derived from biomass or another carbonaceous feedstock.

In some embodiments, the overhead stream includes ethanol and 2-propanol. In some embodiments, the bottoms stream includes 2-propanol and water. The reactive-distillation unit (e.g., distillation column) can include at least one side-draw stream for removing ethanol, 2-propanol, or both ethanol and 2-propanol. The reactive-distillation unit can include at least two side-draw streams.

The reactive-distillation unit, in some embodiments, operates with a temperature profile from about 250° C. or less at the reboiler to about 100° C. or greater at the condenser. In certain embodiments, the reactive-distillation unit operates with a temperature profile from about 235° C. or less at the reboiler to about 125° C. or greater at the condenser.

At least one olefin and water are preferably in countercurrent flow within the reactive-distillation unit. In some embodiments, hydration is rate-limited by water in the first zone and/or the second zone. The first zone is preferably above the second zone so that the first zone for ethylene hydration is at a higher temperature than the second zone for propylene hydration. A stream including ethylene and propylene is preferably introduced to a zone for propylene hydration before contacting a zone for ethylene hydration.

In some embodiments, the feed location to the distillation column is between the first zone and the second zone. Water from the bottoms stream can be recycled to one or more feed locations. A portion of the overhead stream can be refluxed back to the distillation column at a position below the second zone.

When the reactive-distillation unit is a distillation column, the column can include trays, packing, or different column internals. In some embodiments, a portion of the packing comprises an ethylene-hydration catalyst and/or a propylene-hydration catalyst.

This invention further includes an apparatus for producing ethanol and 2-propanol from methanol, the apparatus comprising:

(a) a methanol-to-olefins unit for converting methanol, in the presence of a methanol-to-olefins catalyst, into a first output stream including ethylene and propylene;

(b) a reactive-distillation unit including a first zone containing an propylene-hydration catalyst and a second zone containing a ethylene-hydration catalyst;

(c) an overhead stream from the reactive-distillation unit;

(d) a bottoms stream from the reactive-distillation unit; and (e) means for collecting the ethanol and 2-propanol.

DETAILED DESCRIPTION OF EMBODIMENTS OF THE INVENTION

Figure 1:
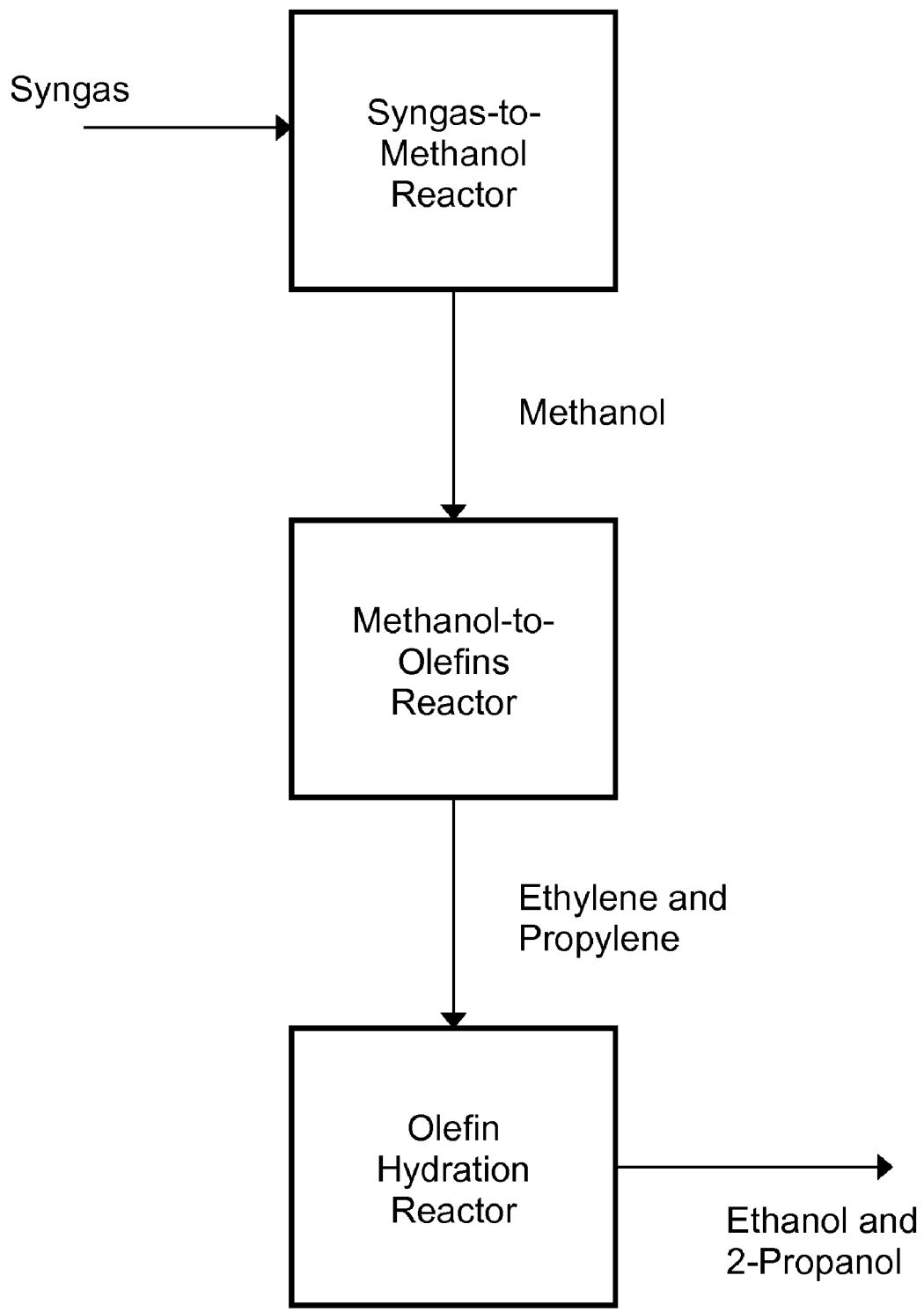
FIG. 1 is a simplified block-flow diagram depicting variations of the invention converting syngas into ethanol and 2-propanol.

This description will enable one skilled in the art to make and use the invention, and it describes several embodiments, adaptations, variations, alternatives, and uses of the invention, including what is presently believed to be the best mode of carrying out the invention.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs.

Unless otherwise indicated, all numbers expressing reaction conditions, stoichiometries, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon the specific analytical technique. Any numerical value inherently contains certain errors necessarily resulting from the standard deviation found in its respective testing measurements.

The present invention will now be described by reference to the following detailed description and figures which characterize and illustrate some preferred embodiments. This description by no means limits the scope and spirit of the present invention.

Some variations of the invention utilize biomass feedstocks for producing syngas. "Biomass" for the purposes of the present invention is any material not derived from fossil resources and comprising at least carbon, hydrogen, and oxygen. Biomass includes, for example, plant and plant-derived material, vegetation, agricultural waste, wood waste, paper waste, animal-derived waste, and municipal solid waste. The present invention can also be used for carbon-containing feedstocks other than biomass, such as a fossil fuel (e.g., coal or petroleum). Thus, any method or system described herein in reference to biomass can alternatively be used with any other carbon-containing feed material.

The methods and systems of the invention can accommodate a wide range of feedstocks of various types, sizes, and moisture contents. In various embodiments, carbon-containing feedstocks can include one or more materials selected from timber harvesting residues, softwood chips, hardwood chips, tree branches, tree stumps, leaves, bark, sawdust, paper pulp, corn stover, wheat straw, rice straw, sugarcane bagasse, switchgrass, miscanthus, animal manure, municipal solid waste, municipal sewage, commercial waste, used tires, grape pumice, almond shells, pecan shells, coconut shells, coffee grounds, grass pellets, hay pellets, wood pellets, cardboard, paper, plastic, rubber, cloth, coal, lignite, coke, lignin, and/or petroleum. Mixtures of any of these feedstocks can be used. Mixtures can be accomplished by blending prior to feeding, co-feeding several feedstocks, or by some other means. A person of ordinary skill in the art will readily appreciate that the feedstock options are virtually unlimited.

In some embodiments of the present invention, syngas passes through a reactor for producing methanol. As is known, methanol can be made at high productivity (such as ~1 kg methanol/kg-catalyst·hr) and these reactors can work at very high syngas conversions. The catalyst could be, for example, a Cu/Zn/Al-based catalyst or another commercial methanol catalyst, including (but not limited to) selection from Cu/ZnO/Al$_2$O$_3$, ZnO/Cr$_2$O$_3$, Cu/ZnO, Cu/ZnO/Cr$_2$O$_3$, Cu/ZrO$_2$, Cu/ThO$_2$, Co/S, Mo/S, Co/Mo/S, Ni/S, Ni/Mo/S, and Ni/Co/Mo/S. In some embodiments, this step employs a low-temperature Cu/Zn/alumina methanol-synthesis catalyst. The temperature of this reactor could be, for example, 230-250° C. and the pressure could be, for example, 750-1000 psi.

In some embodiments, syngas is provided according to methods described in Klepper et al., "Methods and apparatus for producing syngas," U.S. patent application Ser. No. 12/166,167 (filed Jul. 1, 2008); or "Methods and apparatus for producing syngas and alcohols," U.S. patent application Ser. No. 12/166,194 (filed Jul. 1, 2008). U.S. patent application Ser. Nos. 12/166,167 and 12/166,194 are hereby incorporated by reference herein in their entireties.

Preferably, the syngas entering the methanol reactor is compressed. Conditions effective for producing methanol from syngas include reactor pressures from about 20-500 atm, preferably about 50-200 atm or higher. Generally, productivity increases with increasing reactor pressure, and pressures outside of these ranges can be employed with varying effectiveness.

The methanol stream produced from syngas (or a portion of the methanol-containing stream, or another source of methanol) can be passed over a methanol-to-olefin catalyst to generate a mixture of ethylene and propylene. Any suitable methanol-to-olefin catalyst can be employed. That is, any material exhibiting activity for converting methanol to one or more olefins can be employed.

In some embodiments, the methanol-to-olefin catalyst comprises an aluminosilicate zeolite, such as one selected from the group consisting of ZSM-5, ZSM-11, ZSM-12, ZSM-23, ZSM-35, and ZSM-48.

In some embodiments of the invention, the methanol-to-olefin catalyst comprises a silicoaluminophosphate ("SAPO"), such as a SAPO selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, and SAPO-56.

SAPOs can be synthesized by forming a mixture containing sources of silicon, aluminum, and phosphorus mixed with an organic template, and then crystallizing the molecular sieve at reaction conditions. Many factors affect the form the molecular sieve takes, including the relative amounts of the different components, the order of mixing, the reaction conditions (e.g. temperature and pressure) and the choice of organic template.

A preferred methanol-to-olefin catalyst that can be used is SAPO-34 (also referred to herein as H-SAPO-34). The preparation of SAPO-34 is known in the art, as exemplified in U.S. Pat. No. 4,440,871, issued to Union Carbide on Apr. 3, 1984, which is incorporated by reference herein in its entirety. SAPO-34 has a three-dimensional microporous crystal framework structure and an empirical composition on an anhydrous basis of $(Si_xAl_yP_z)O_2$ where x, y and z represent the mole fractions of silicon, aluminum, and phosphorus, respectively, and where typically $x+y+z=1$.

Without being limited by any hypothesis, it is believed that the framework structure can trap organic intermediates (such as ethylbenzenes) deriving from methanol. These organic intermediates act as organic reaction centers that catalyze the olefin-forming reactions in cooperation with active sites over the surface of the catalyst. Olefins, such as ethylene and propylene, are small enough to exit the micropores of SAPO-34.

SAPO-34 offers a good combination of catalyst activity, selectivity, and durability. Ethylene/propylene ratios in H-SAPO-34 may be driven by increased temperatures; at higher temperatures ethylene selectivities increase. At higher temperatures, coking rates are higher so more frequent regeneration is typically needed.

It can be further beneficial for the methanol-to-olefin catalyst to employ silicoaluminophosphates that also include at least one transition metal. Preferably, the transition metal is selected from manganese, nickel, or cobalt. The process of incorporating the transition metal may be accomplished through any one of the standard methods well known to those skilled in the art. In one embodiment, a solution of the desired metal is first made by dissolving the desired amount of the metal-containing compound in water under mild conditions. The temperature of mixing is dependent upon the solubility of the metal compound in water, or another medium.

The amount of metal which is incorporated may vary over a wide range depending, at least in part, on the selected silicoaluminophosphate (or other material) and on the incorporation method. The amount of metal incorporated is measured on an atomic metal basis in terms of silicon-to-metal ratio. The silicon-to-metal atomic ratios are in the range from about 0.1:1 to about 1000:1, preferably from about 1:1 to about 500:1, and most preferably from about 10:1 to about 200:1.

In some embodiments wherein nickel is the selected transition metal, high methanol-to-olefin conversion can be accomplished by using Ni-SAPO-34. For example, use of Ni-SAPO-34 is described in Inui and Kang, "Reliable procedure for the synthesis of Ni-SAPO-34 as a highly selective catalyst for methanol to ethylene conversion," *Applied Catalysis A: General*, vol. 164, 211-223, 1997. As taught therein, ethylene selectivity is 88% over Ni-SAPO-34, at 425-450° C. and close to atmospheric pressure.

In some embodiments, ethylene is the preferred olefin. In other embodiments, propylene is the preferred olefin. In some embodiments, it is preferred to product higher quantities of $C_{3+}$ olefins, including propylene, butenes (e.g., 1-butene and 2-butene), and optionally higher olefins. Generally, process conditions and catalysts can be selected to optimize selectivity to one particular olefin, which can be ethylene or propylene in particular embodiments. Or, process conditions and catalysts can be selected to optimize selectivity to total olefins rather than non-olefins (e.g., alkanes, aromatics, and $CO_2$). Process conditions and catalysts can also be selected to maximize methanol conversion, maximize yield of total olefins, maximize yield of $C_2$-$C_3$ olefins, or maximize yield of a specific olefin such as ethylene or propylene.

Preferably, methanol is completely or nearly completely converted in the olefin-forming process step. In various embodiments, selectivities to ethylene are in the 50-75 mol % range, while selectivities to propylene are in the 25-50 mol % range. In preferred embodiments, negligible quantities of methane and carbon dioxide are produced during olefin formation. Production of carbon dioxide can occur, however, in the gas phase away from catalyst surfaces, or possibly catalyzed by other non-selective surfaces present, such as walls of the reactor.

The olefin-forming reaction is exothermic. The catalyst can produce coke, and if that occurs, the catalyst can be periodically regenerated by hot air or oxygen. A plurality of reactors can be employed, so that when one is being regenerated, the other reactors can continue operation.

The temperature for the olefin-forming step(s) can be 375-425° C., for example. Higher temperatures will generally lead to higher selectivity to ethylene relative to propylene, but the choice of catalyst will also dictate product distribution. Any pressure can be employed, and selection of pressure will typically be dictated by economics and integration with an overall process. Reactor configurations are further discussed below.

The olefins produced from methanol can be passed through a catalyst to hydrate the olefins, by water addition across the double bonds. Acid catalysts, such as phosphoric acid, can be effective for olefin hydration. Hydration will proceed without any catalyst, but olefin hydration is preferably catalyzed to increase rates, maximize alcohol yield, and minimize olefin polymerization or other undesirable side reactions. The temperature for this third step can be 100-250° C., for example. In some embodiments, ethylene is hydrated at about 240° C. while propylene is hydrated at about 195° C. At excessively high temperatures, olefin polymers have a tendency to form.

Figure 2:
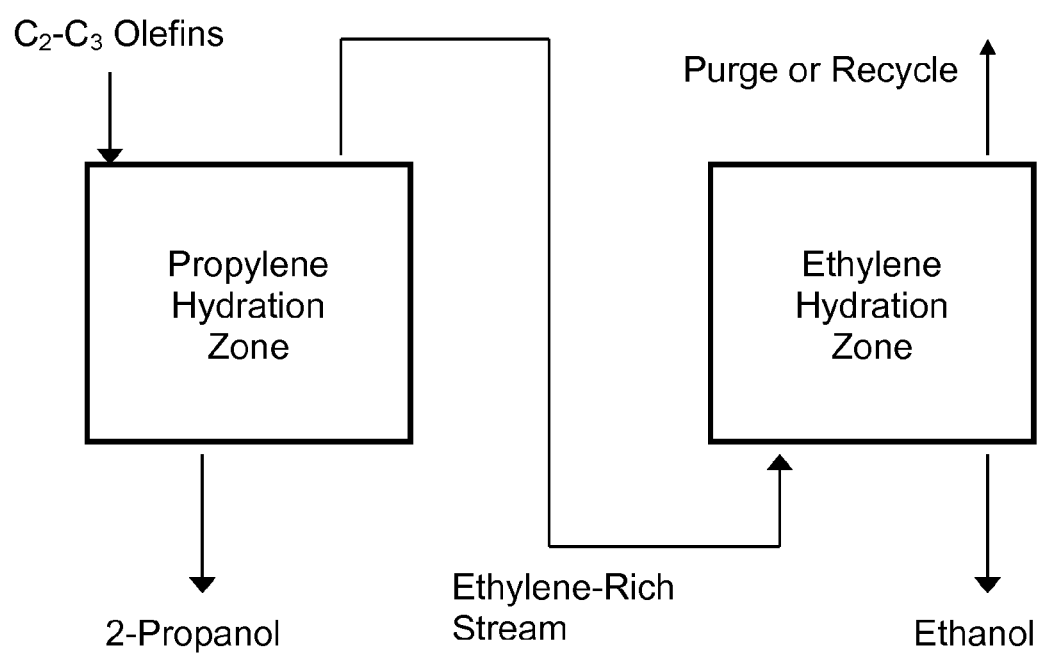
FIG. 2 is a simplified block-flow diagram of some variations wherein propylene hydration is followed by ethylene hydration.

When the aforementioned process steps are conducted in combination, such as summarized in FIGS. 1 and 2, the process generally produces a composition comprising ethanol and propanol. The propanol can include both 1-propanol and 2-propanol, although hydration of propylene typically generates 2-propanol in accordance with Markovnikov's rule. The secondary alcohol 2-propanol is also known as propan-2-ol, isopropyl alcohol, isopropanol, or IPA. By varying process conditions and catalysts, the product distribution can be adjusted to favor ethanol or to favor propanol, depending on what is desired. In some embodiments, ethanol is the dominant product of the overall process. In other embodiments, 2-propanol is the dominant product of the overall process.

Methanol-to-olefin catalysts, such as H-SAPO-34, will generally make a small amount of linear butenes that will hydrate to 2-butanol. The range of temperatures of these hydration reactions, for direct hydration processes utilizing heterogeneous catalysts, is typically from about 100-250° C. with heavier olefins (e.g., propylene and butenes) being hydrated at lower temperatures. When hydrated in separate reactors, two or three hydration reactors are contemplated (see, for example, FIG. 2). Alcohols can be isolated by condensation or by scrubbing into a suitable solvent, which can be water, DME, or propane (U.S. Pat. No. 4,469,903).

Typically, a hydration reaction produces an alcohol, or a product mixture comprising an alcohol and an ether, the alcohol and the ether each having the same carbon chain length as the olefin, in equilibrium with the olefin and water. The thermodynamics and hence the equilibrium of the hydration reaction is such that formation of the alcohol is more favorable at low temperatures and high pressures.

In some embodiments, at least a portion of the water necessary for hydration of ethylene (or other olefins) is supplied from the methanol-to-olefins step, which produces water during dehydration. Preferably, such water is supplied while substantially still hot, thereby improving overall thermal efficiency.

Although capital and operating costs are lower when the hydration reaction is performed under mild conditions, the equilibrium amount of the alcohol in the reaction mixture at low pressures is lower than the equilibrium amount of alcohol in the reaction mixture at high pressures. Several catalysts having acidic properties are useful for the hydration of an olefin to the corresponding alcohol. Such catalysts include acidic cation-exchanged resins, inorganic acids, and acids supported on inorganic supports. In some embodiments, olefin-hydration catalysts are selected from zeolites, supported acids (e.g., phosphoric acid on silica), acidic resins, and heteropoly acids. The ethylene-hydration catalyst can be the same as, or different from, the propylene-hydration catalyst.

Various heterogeneous catalysts may be used for hydration of olefins. Ethylene may be hydrated, typically at temperatures above 200° C., by $H_3PO_4$/$SiO_2$ catalysts. This type of catalyst is the basis of the Shell ethylene-hydration process, the first direct catalytic hydration process known commercially. Carbons may be used instead of silica as a support for phosphoric acid. Alumina is less preferred as a support for phosphoric acid since relatively inert $AlPO_4$ will tend to form.

Zeolites, such as H-ZSM-5, H-mordenite, H-Beta, or H—Y, may also be used as hydration catalysts in some embodiments. When H—Y is used, preferably its Si/Al is preferably greater than 10 and preferably at least 25% of Al is associated with a Brønsted acid site. H-ZSM-5 or H-mordenite are preferable. Si/Al ratios can be in the range of 50-100, in some embodiments. For H-ZSM-5, a mild dealumination is preferable in order to generate a suitable fraction of strongly acidic sites. Dealumination may be conducted by various means, such as treatment with steam, leaching with mineral acid or organic acids such as oxalic acid, or treatment with $SiCl_4$ and the like. An advantage of medium-pore zeolites (such as ZSM-5, H-mordenite, and the like) is that the pores are large enough to accommodate reactant olefins and water, as well as product alcohols, but small enough to prevent ethers from forming.

Acidic resins based on polysiloxane can be used in some embodiments. In certain embodiments, thermally durable silica-Nafion® composite resins are employed. Supported heteropoly acid catalysts may also be used. Aqueous solutions of heteropoly acids also may be used in some embodiments. Zeolites may be used to catalyze these hydration reactions.

More reactive olefins, such as propene and butenes, may be hydrated over strong acid organic resins such as Nafion resins. These resins are unstable above about 150° C., so they are not preferred for ethylene hydration. Ethylene, propene, and butenes may be hydrated by aqueous mixtures of suitable polytungate acids, such as (but by no means limited to) $H_3PW_{12}O_{40}$, $H_4SiW_{12}O_{40}$, or by their molybdenum analogues.

In other variations of the invention, indirect hydration of olefins is employed. A mixture of olefins (mainly ethylene and propylene, but also small amounts of butenes will typically be present) may hydrated indirectly by initial absorption into sulfuric acid and subsequent hydrolysis of the resultant sulfate esters. This indirect hydration method has been practiced for ethylene hydration (e.g., Carle and Stewart, "Synthetic Ethanol Production," *Chemistry and Industry*, pp. 830-839, 1962). Similarly, indirect hydration has been used to make isopropanol from propene (e.g., U.S. Pat. No. 3,352,930). Advantages of this approach include the following: a mixture of olefins may be hydrated more or less simultaneously; and thermodynamic limitations associated with direct hydration are avoided, allowing very high conversion of olefins.

Indirect hydration with sulfuric acid is thought to operate as follows. One or two olefins add to sulfuric acid, making the corresponding sulfate esters. Some reactions describing this step of the process are as follows:

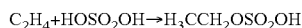

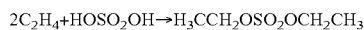

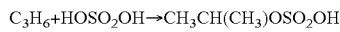

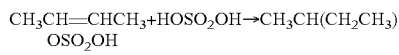

These sulfate esters are then hydrolyzed to alcohol and sulfuric acid, which may be described as follows for the ethyl-sulfate:

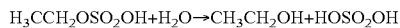

If the reaction temperature is too high, olefin polymers may form. Ethers (both symmetrical and nonsymmetrical) also may form. Also, $SO_2$ can form to a limited extent. Dilute sulfuric acid that is formed must be reconcentrated.

In preferred embodiments, alcohols formed from olefins are isolated and purified. Alcohols can be separated from unreacted olefin streams by selective absorption of alcohol into water. The aqueous alcoholic mixture is then separated in a series of distillation columns, often including an azeotropic distillation. A similar approach may be used to separate the mixture of product alcohols from unreacted olefins from the sulfuric acid/water indirect-hydration reactor.

Instead of absorption of product alcohols into water (which involves formation of undesired azeotropes whose resolution is energy intensive), alcohols can be absorbed into a dialkyl ether such as dimethyl ether. Dimethyl ether is conveniently available in a methanol-based biorefinery, since methanol is readily dehydrated selectively, under mild conditions, over catalysts such as H-ZSM-5, Na,H-ZSM-5, or $\gamma$-$Al_2O_3$ to dimethyl ether (DME). The absorption can be done under moderate pressure and low temperature, conditions under which dimethyl ether is a liquid. Purification of the resultant mixtures is straightforward since DME may be removed by volatilization, resulting in a non-aqueous mixture of alcohols more amenable to separation by distillation.

In some variations of this invention, reaction and separation are carried out simultaneously in a reactive-distillation unit, such as a column. Reactive distillation can reduce energy costs and is especially useful for equilibrium-limited reactions due to continuous removal of products from the reaction zone.

In some embodiments, a reactive-distillation unit employs one or more acid catalysts deployed in at least two separate beds, to hydrate mixtures of olefins whose hydration catalysis preferably proceeds at different temperatures. Use of more active acid catalysts may allow ethylene hydration to proceed at considerably lower temperatures. Decreasing the temperatures of ethylene hydration decreases the severity of thermodynamic limitations which should enable higher levels of ethylene conversion.

The ethylene conversion bed is preferably below the propylene conversion bed. Makeup olefins (i.e., from column reflux, plant recycle, or fresh feed) are preferably introduced near the bottom of their respective beds. Olefins can be purified, at least in part, prior to being fed back into the unit. Water is preferably introduced near the top of one or both of the olefin-hydration beds. In some embodiments, the unit is operated so that essentially all water is consumed in hydration reactions.

The reactive-distillation unit can be operated at sufficient pressure to encourage forward reaction (hydration) by Le Chatlier's principle and also permit product alcohols to exist as both liquid and vapor. In some embodiments, olefins and water are fed countercurrently in each reaction zone and reactions are performed under water-limiting conditions in order to keep the bulk of the reactor essentially anhydrous.

In some embodiments, alcohols are collected from the bottoms stream, while unreacted olefins are collected from the overhead stream. In some embodiments, there is a split of alcohols, e.g., ethanol is collected in the overhead stream and 2-propanol is collected from the bottoms stream. Water is expected to collect in the bottoms stream.

Figure 3:
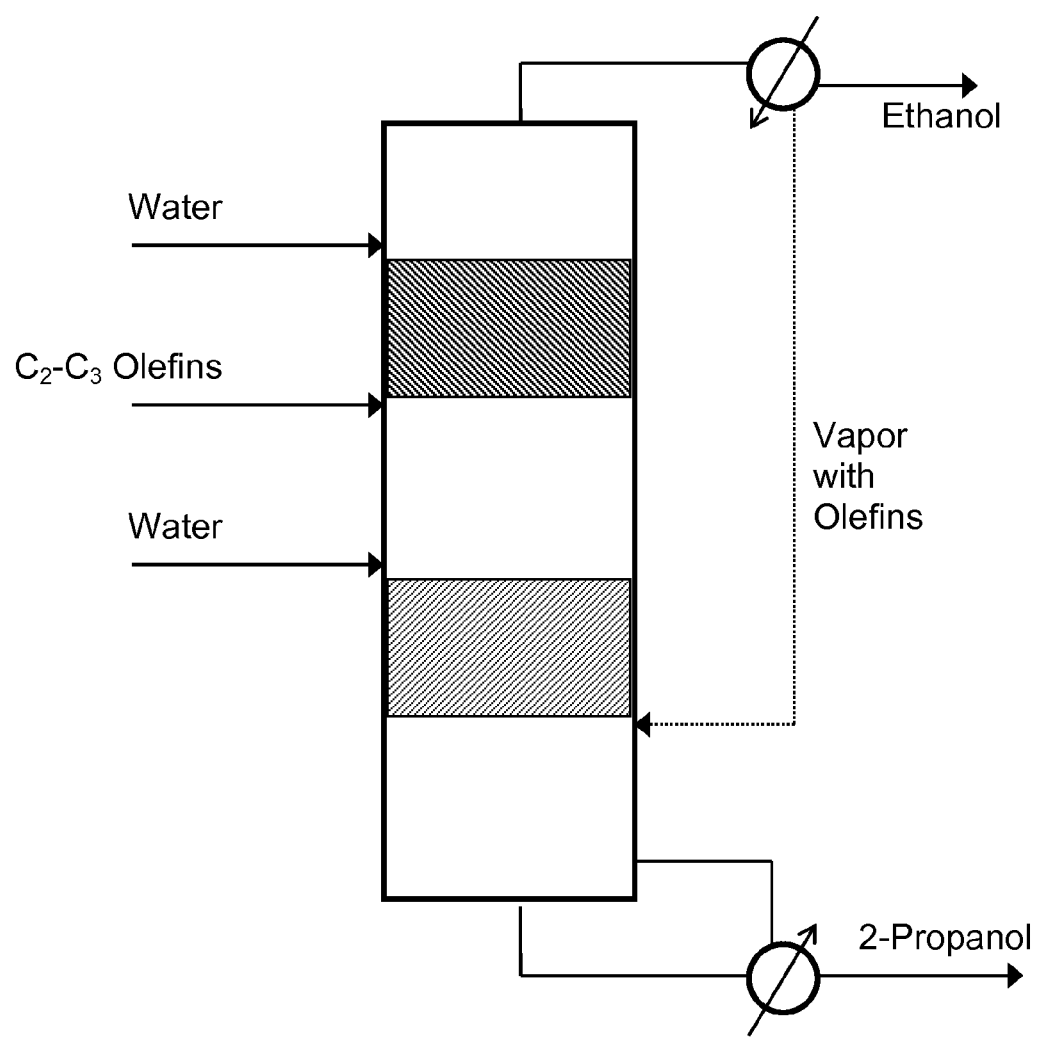
FIG. 3 is a sketch of a reactive-distillation unit according to some embodiments of the invention.

FIG. 3 is an exemplary (and non-limiting) reactive-distillation unit wherein ethylene and propylene are introduced below the propylene-hydration zone (upper shaded portion). Water is introduced above each of the hydration zones in FIG. 3. In other embodiments, water is fed to only one of these locations; in still other embodiments, water is fed to additional locations beyond the two feed locations depicted in FIG. 3. In the condenser, the liquid phase comprises ethanol and can be recovered, while the vapor phase comprises unreacted olefins which can be fed back into the column below the ethylene-hydration zone (lower shaded portion). In the bottoms, the liquid stream comprises 2-propanol which can be recovered. Due to the chemical kinetics involved, the vapor recycle from the condenser can be enriched in ethylene which is why it can be preferred to feed this vapor reflux at or below the ethylene-hydration zone.

Figure 4:
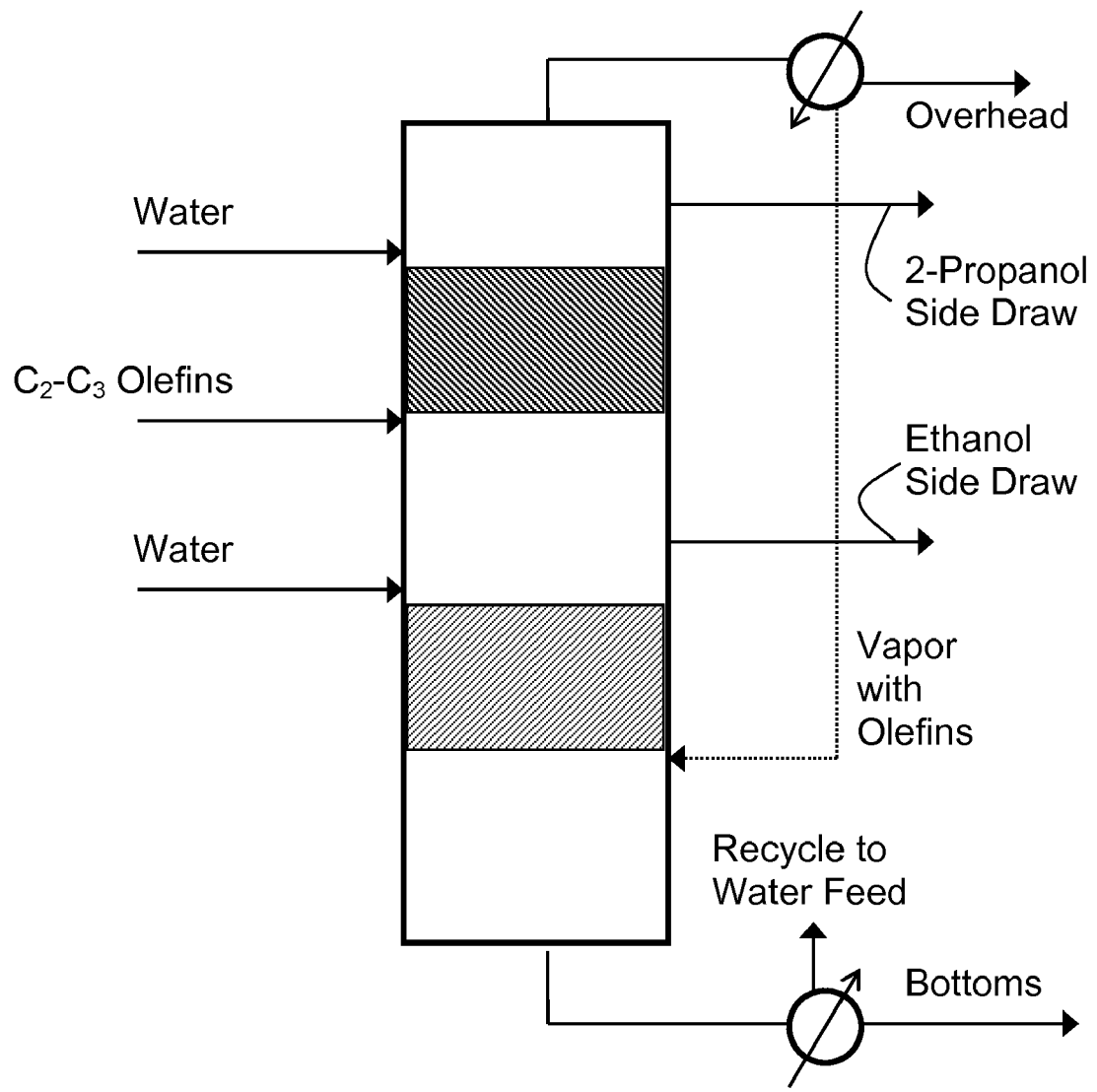
FIG. 4 is a sketch of a reactive-distillation unit according to some embodiments of the invention.

FIG. 4 is another exemplary (and non-limiting) reactive-distillation unit wherein ethylene and propylene are introduced below the propylene-hydration zone (upper shaded portion). Water is introduced above each of the hydration zones in FIG. 4. The vapor stream from the condenser can be recycled in a similar manner as described above for FIG. 3. Water in the bottoms can be recycled to one or more water-feed locations. In this embodiment, two side-draw streams are included: a 2-propanol-containing side draw stream that withdraws material between the propylene-hydration zone and the condenser; and an ethanol-containing side-draw stream that withdraws material between the two hydration zones. Of course, other locations for side-draw streams are possible.

The reactive-distillation unit can contain packing in addition to one or more catalysts. In some embodiments, column packing is coated, or impregnated, with hydration catalysts. Catalysts can be wrapped in fabric and inserted into the column internals. Or, catalysts can be placed on one or more trays within a distillation column.

For the purpose of the present invention, a "reactor" is any apparatus capable of being effective for catalyzing the conversion of reactants to products. A reactor can be a single vessel or a plurality of vessels, i.e. a network of several reactors in various arrangements.

The reactors employed herein can be engineered and operated in a wide variety of ways. Reactor operation can be continuous, semicontinuous, or batch. Operation that is substantially continuous and at steady state is preferable. The flow pattern can be substantially plug flow, substantially well-mixed, or a flow pattern between these extremes. The flow direction can be vertical-upflow, vertical-downflow, or horizontal.

The catalyst phase within each reactor can be a packed bed or a fluidized bed. In some embodiments, the methanol-to-olefin reactor employs a fluidized bed. The hydration reactor can also employ a fluidized bed if suitable catalyst materials are utilized. That is, fluidized beds are not particularly suitable for acidic resins or for phosphoric acid catalysts.

The catalyst particles can be sized and configured such that the chemistry is, in some embodiments, mass-transfer-limited or kinetically limited. The catalyst can take the form of a powder, pellets, granules, beads, extrudates, and so on. When a catalyst support is optionally employed, the support may assume any physical form such as pellets, spheres, monolithic channels, etc. The supports may be coprecipitated with active metal species; or the support may be treated with the catalytic metal species and then used as is or formed into the aforementioned shapes; or the support may be formed into the aforementioned shapes and then treated with the catalytic species.

Some embodiments employ heat integration such that process heat from one or more exothermic steps is used to provide heat for distillation (or other purification) of the desired final products. Alternatively, or additionally, such heat can supply energy for the conversion of a carbon-containing feedstock into syngas, such as in gasification.

In general, the specific selection of reactor configuration, feed compositions, temperatures, pressures, and residence times (or feed rates) for each reactor, reaction zone, or distillation column will be selected to provide an economically optimized process. The plurality of reactor variables and other system parameters can be optimized, in whole or in part, by a variety of means.

The quantity of liquid alcohols that can be generated from a given amount of biomass (or other carbonaceous feedstock) will depend on the syngas-generation process selected, the specific feedstock, the selection of process conditions and catalysts for the methods of the present invention, and various engineering and economic considerations relating to the overall process and biorefinery site (e.g., utilities available). In some exemplary embodiments, the feedstock is wood which is typically about 50 wt % carbon.

For example, it can be desired to operate in a self-sufficient manner, wherein a portion of biomass, syngas, and/or methanol are converted to energy to supply to the process, rather than to convert to liquid alcohols. In these variations, the final yields of alcohols may be reduced but the process may be preferable from economic and environmental viewpoints. To operate in a self-sufficient manner, in various embodiments, about 30%, 40%, or 50% of the energy content of the starting feedstock is converted to energy.

When it is desired to operate in a self-sufficient manner, the present invention can be carried out to generate $C_2$-$C_3$ alcohol yields of at least about 50, 60, 70, 75, or more gallons per dry ton of feedstock. When it is desired to maximize the yields of alcohols and utilize a separate source of energy (e.g., natural gas), the present invention can be carried out to generate $C_2$-$C_3$ alcohol yields of at least about 100, 110, 120, 125, or more gallons per dry ton of feedstock.

The distribution of alcohols produced can be adjusted to favor ethanol or to favor 2-propanol, as taught hereinabove. For example, a SAPO-34 catalyst can generate $C_2$ and $C_3$ olefins at selectivities described in Wilson and Barger, *Microporous and Mesoporous Materials*, vol. 29, pp. 117-126, 1999. After effective hydration, the expected products from 1 dry ton include about 35 gallons ethanol, 30 gallons 2-propanol, and 7 gallons 2-butanol when the methanol-to-olefins step is conducted at about 375° C. When the methanol-to-olefins step is instead conducted at about 450° C., the expected products from 1 dry ton include about 50 gallons ethanol, 20 gallons 2-propanol, and 4 gallons 2-butanol. These yields assume that 40% of the starting biomass is used for energy production.

If, instead, a separate source of process energy is employed, yields can be higher. A SAPO-34 catalyst can generate $C_2$ and $C_3$ olefins at selectivities described in Wilson and Barger, *Microporous and Mesoporous Materials*, vol. 29, pp. 117-126, 1999. After effective hydration, the expected products from 1 dry ton include about 60 gallons ethanol, 50 gallons 2-propanol, and 12 gallons 2-butanol when the methanol-to-olefins step is conducted at about 375° C. When the methanol-to-olefins step is instead conducted at about 450° C., the expected products from 1 dry ton include about 85 gallons ethanol, 33 gallons 2-propanol, and 6 gallons 2-butanol.

When Ni-SAPO-34 is employed to maximize ethanol production, as described hereinabove, the ethanol yield from 1 dry ton of biomass is expected to be about 70 gallons in the energy self-sufficient mode of operation (assuming 40% of the starting biomass is used for energy production). Under conditions to maximize ethanol yield per ton of biomass, the ethanol yield from 1 dry ton of biomass is expected to be about 115 gallons along with 5 gallons of 2-propanol. These yield projections are based on methanol-to-olefin selectivities provided in Inui and Kang, *Applied Catalysis A: General*, vol. 164, pp. 211-223, 1997.

Conventional distillation methods, well-known in the art, can be used to distill the final product. Any number of distillation columns may be employed, depending on the desired overall separation. In some embodiments, a purified ethanol product can be made to meet the ASTM D4806-07a specification for fuel ethanol, or some other fuel-grade specification as will be appreciated. In some embodiments, a purified 2-propanol product is produced.

The purified alcohol product can be used to power an internal combustion engine to power a transportation vehicle. In some embodiments, the purified alcohol(s) product can be combined (blended) with at least one other hydrocarbon, or multiple hydrocarbons such as gasoline, to create a liquid-fuel blend. In some embodiments, a mixture of ethanol and 2-propanol is produced as an alcohol product. This biofuel mixture can be blended into gasoline to meet oxygenate requirements, while decreasing the Reid vapor pressure of the liquid fuel relative to gasoline blends with ethanol as the primary oxygenate. 2-Propanol can also counteract water problems in fuel tanks that can accompany ethanol/gasoline blends (2-propanol is able to dissolve small quantities of water in fuel tanks).

In some embodiments, one or more alcohols produced, such as 2-propanol, can be sold into the chemical markets. For example, 2-propanol is used widely as in solvent, cleaning, and drying applications.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

All publications, patents, and patent applications cited in this specification are herein incorporated by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent will cover those variations as well. The present invention shall only be limited by what is claimed.

What is claimed is:

1. A method for producing ethanol and 2-propanol from methanol, said method comprising:
    (a) converting methanol, in the presence of a methanol-to-olefins catalyst, into a stream including ethylene and propylene;
    (b) feeding said stream from step (a) and water to a reactive-distillation unit including a first zone containing an propylene-hydration catalyst, a second zone containing a ethylene-hydration catalyst, an overhead stream, and a bottoms stream;
    (c) operating said reactive-distillation unit under effective conditions for hydration of propylene to 2-propanol in said first zone and ethylene to ethanol in said second zone; and
    (d) recovering ethanol and 2-propanol in one or more exit streams from said reactive-distillation unit.

2. The method of claim 1, wherein said methanol is derived from syngas.

3. The method of claim 2, wherein said syngas is derived from biomass.

4. The method of claim 1, wherein said methanol-to-olefins catalyst comprises an aluminosilicate zeolite.

5. The method of claim 4, wherein said aluminosilicate zeolite is selected from the group consisting of ZSM-5, ZSM-11, ZSM-12, ZSM-23, ZSM-35, and ZSM-48.

6. The method of claim 1, wherein said methanol-to-olefins catalyst comprises a silicoaluminophosphate.

7. The method of claim 6, wherein said silicoaluminophosphate is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, and SAPO-56.

8. The method of claim 7, wherein said silicoaluminophosphate is SAPO-34.

9. The method of claim 6, wherein said silicoaluminophosphate further includes one or more transition metals.

10. The method of claim 9, wherein said one or more transition metals is selected from the group consisting of Mn, Ni, and Co.

11. The method of claim 10, wherein said silicoaluminophosphate includes Ni.

12. The method of claim 11, wherein said methanol-to-olefins catalyst is Ni-SAPO-34.

13. The method of claim 9, wherein the ratio of silicon to said transition metal is selected from about 1 to about 500.

14. The method of claim 13, wherein said ratio is selected from about 10 to about 200.

15. The method of claim 1, wherein in step (a), the molar ratio of ethylene to propylene is greater than about 2.

16. The method of claim 15, wherein in step (a), said molar ratio of ethylene to propylene is greater than about 10.

17. The method of claim 1, wherein said ethylene-hydration catalyst is selected from zeolites, supported acids, acidic resins, and heteropoly acids.

18. The method of claim 1, wherein said propylene-hydration catalyst is selected from zeolites, supported acids, acidic resins, and heteropoly acids.

19. The method of claim 1, wherein said ethylene-hydration catalyst and/or said propylene-hydration catalyst are each selected from zeolites.

20. The method of claim 1, wherein at least a portion of water produced from reactions during step (a) is fed to said reactive-distillation unit during step (b).

21. The method of claim 20, wherein all of said water produced during step (a) is fed to said reactive-distillation unit during step (b).

22. The method of claim 1, wherein said overhead stream includes ethanol and 2-propanol.

23. The method of claim 1, wherein said bottoms stream includes 2-propanol and water.

24. The method of claim 1, wherein said reactive-distillation unit includes at least one side-draw stream for removing ethanol, 2-propanol, or both ethanol and 2-propanol.

25. The method of claim 24, wherein said reactive-distillation unit includes at least two side-draw streams.

26. The method of claim 1, wherein said reactive-distillation unit operates with a temperature profile from about 250° C. or less at the reboiler to about 100° C. or greater at the condenser.

27. The method of claim 26, wherein said reactive-distillation unit operates with a temperature profile from about 235° C. or less at the reboiler to about 125° C. or greater at the condenser.

28. The method of claim 1, wherein at least one olefin and water are in countercurrent flow within said reactive-distillation unit.

29. The method of claim 1, wherein hydration is rate-limited by water in said first zone and/or said second zone.

30. The method of claim 1, wherein said reactive-distillation unit is a distillation column.

31. The method of claim 30, wherein said first zone is above said second zone.

32. The method of claim 30, wherein the feed location to said distillation column is between said first zone and said second zone.

33. The method of claim 30, wherein said stream including ethylene and propylene is introduced to a zone for propylene hydration before contacting a zone for ethylene hydration.

34. The method of claim 1, comprising recovering water from the bottoms stream and recycling at least a portion of said water to step (b).

35. The method of claim 30, wherein said distillation column employs trays.

36. The method of claim 30, wherein said distillation column employs packing.

37. The method of claim 36, wherein a portion of said packing comprises an ethylene-hydration catalyst.

38. The method of claim 36, wherein a portion of said packing comprises a propylene-hydration catalyst.

39. The method of claim 30, wherein a portion of said overhead stream is refluxed back to said distillation column at a position below said second zone.

40. The method of claim 1, further comprising generating butenes during step (a).

41. The method of claim 40, further comprising hydrating said butenes to 2-butanol during step (c).

42. The method of claim 1, wherein during step (c), one or more dialkyl ethers are generated, and wherein said method further comprises recovering at least a portion of said dialkyl ethers from said reactive-distillation unit.

* * * * *